(12) United States Patent
Fukasawa et al.

(10) Patent No.: US 10,493,036 B2
(45) Date of Patent: Dec. 3, 2019

(54) ENTERIC CAPSULE

(71) Applicant: SUNSHO PHARMACEUTICAL CO. LTD, Fuji-shi, Shizuoka (JP)

(72) Inventors: Takayuki Fukasawa, Fuji (JP); Kenichi Koyama, Fuji (JP); Tomoya Suzuki, Fuji (JP)

(73) Assignee: SUNSHO PHARMACEUTICAL CO. LTD, Fuji-shi (JP)

(*) Notice: Subject to any disclaimer, the term of this patent is extended or adjusted under 35 U.S.C. 154(b) by 22 days.

(21) Appl. No.: 15/748,140

(22) PCT Filed: Aug. 10, 2016

(86) PCT No.: PCT/JP2016/073617
§ 371 (c)(1),
(2) Date: Jan. 26, 2018

(87) PCT Pub. No.: WO2017/030072
PCT Pub. Date: Feb. 23, 2017

(65) Prior Publication Data
US 2018/0221288 A1    Aug. 9, 2018

(30) Foreign Application Priority Data

Aug. 19, 2015 (JP) .................... 2015-161910

(51) Int. Cl.
| | | |
|---|---|---|
| *A61K 9/48* | (2006.01) | |
| *A61K 47/36* | (2006.01) | |
| *A61K 47/42* | (2017.01) | |
| *A61K 8/11* | (2006.01) | |
| *A61K 8/73* | (2006.01) | |
| *A61K 8/64* | (2006.01) | |

(52) U.S. Cl.
CPC .............. *A61K 9/4825* (2013.01); *A61K 8/11* (2013.01); *A61K 8/64* (2013.01); *A61K 8/73* (2013.01); *A61K 9/48* (2013.01); *A61K 9/4808* (2013.01); *A61K 9/4891* (2013.01); *A61K 47/36* (2013.01); *A61K 47/42* (2013.01)

(58) Field of Classification Search
None
See application file for complete search history.

(56) References Cited

U.S. PATENT DOCUMENTS

| | | | |
|---|---|---|---|
| 5,958,450 A * | 9/1999 | Tashiro ............... | A61K 9/4816 424/451 |
| 2003/0044456 A1 | 3/2003 | Ichie et al. | |
| 2006/0088590 A1* | 4/2006 | Sukuru ............... | A61K 9/4816 424/456 |
| 2006/0292212 A1* | 12/2006 | Paris .................... | A61K 9/4816 424/451 |

FOREIGN PATENT DOCUMENTS

| | | |
|---|---|---|
| JP | H07-145082 A | 6/1995 |
| JP | H11-76369 A | 3/1999 |
| JP | 2009-196961 A | 9/2009 |
| JP | 2010-47548 A | 3/2010 |
| WO | 00/24267 A1 | 5/2000 |
| WO | 2011/048388 A2 | 4/2011 |
| WO | 2013/100013 A1 | 7/2013 |
| WO | 2015/195989 A1 | 12/2015 |

OTHER PUBLICATIONS

Sep. 6, 2016 Search Report issued in International Patent Application No. PCT/JP2016/073617.

* cited by examiner

*Primary Examiner* — Craig D Ricci
*Assistant Examiner* — Dominic Lazaro
(74) *Attorney, Agent, or Firm* — Oliff PLC

(57) ABSTRACT

A capsule excellent in enteric property with the assumption that gelatin is used as a main base material of the capsule coating. An alkali-treated gelatin and carrageenan are contained as base materials of the capsule coating. In the gastric (aqueous) environment, the alkali-treated gelatin which is positively (+) charged coexists with the carrageenan which is negatively (−) charged, and amino groups (NH4+) in the gelatin react with sulfate groups (SO3−) in the carrageenan so that the capsule coating is insolubilized. On the other hand, in the intestinal (aqueous) environment, the alkali-treated gelatin which is negatively (−) charged coexists with the carrageenan which is negatively (−) charged, and the amino groups (NH4+) in the gelatin are repulsive to the sulfate groups (SO3−) in the carrageenan so that the capsule coating quickly disintegrates and dissolves.

15 Claims, No Drawings

ENTERIC CAPSULE

TECHNICAL FIELD

The present invention relates to a capsule that contains a food, a medicament, a quasi-drug, or the like as an effective ingredient and that is suitable for releasing such an ingredient in a body, and particularly to an enteric capsule, which utilizes an enteric property, that is, a property of not dissolving in the stomach but dissolving in the intestines to release the content therein.

BACKGROUND ART

In general, gelatin is widely used since it has many advantages as a base material of a capsule coating, such as reversible sol-gel transformation by a temperature change, normal gelation temperature, excellent film formability, high mechanical strength of formed film, solubility in a body, high nutritional value of itself, and absorbability in a body.

Incidentally, when a capsule for medicament quickly dissolves in acidic secretions in the stomach, the medicament is released in the stomach, which is not preferable in terms of side effects thereof, persistence of the drug action, and the like.

From these viewpoints, various enteric capsules have conventionally been proposed.

In one example, a surface of a capsule coating is coated with an enteric polymer material, such as zein, shellac, and Eudragit to make a tri-layered structure. However, it is difficult to strictly control the conditions in the coating process, and difference in the coating layer thickness among lots, unevenness in a coating layer of each capsule, or peeling of a coating layer, and the like arise depending on the technical level of the worker, possibly causing variation in the enteric function.

On the other hand, examples of a capsule coating that imparts the enteric property without any coating process include a gelatin-based capsule coating having a low methoxyl pectin incorporated therein as described in PTL 1. However, a low methoxyl pectin is insolubilized in the presence of divalent or monovalent cations. Thus, when the capsule content contains divalent or monovalent cations, it is difficult to control the enteric property and the raw materials to be incorporated in the capsule content are restricted in production of a capsule formulation. In addition, when the content containing divalent or monovalent cations is used for a capsule formulation, the content possibly fails to be absorbed in the body due to the delayed disintegration in the intestines.

CITATION LIST

Patent Literature

PTL 1: JP-A-2010-47548
PTL 2: JP-A-07-145082

SUMMARY OF INVENTION

Technical Problem

In a formulation proposed in PTL 2, gelatin is used as a main base material of a capsule coating and carrageenan is used together, and the pH of a coating solution is adjusted between 5 and 3. When this procedure is actually implemented, gelatin and carrageenan aggregate and settle down in the stage of the coating solution to lower the gal strength. Accordingly, the content leaks or the capsule deforms, particularly in production of a soft or seamless capsule formulation, making stable continuous production difficult.

Thus, an object of the present invention is to provide a novel and useful enteric capsule that can solve the above problem.

Solution to Problem

As a result of trial and error, the present inventors have found that, by incorporating an alkali-treated gelatin and carrageenan as base materials of a capsule coating, the coating is insolubilized in the acidic range and quickly dissolves in the alkaline range whether or not the capsule content contains divalent or monovalent cations, and that an alkali-treated gelatin and carrageenan can be incorporated not only into the coating side but also into the coated side depending on the composition, and can impart the enteric property to the coated side if incorporated.

On the basis of the findings, the present inventors have come up with a novel and useful enteric capsule that can also solve the above problem.

That is, the enteric capsule of the present invention is characterized by containing an alkali-treated gelatin and carrageenan as an enteric property imparting agent in the capsule coating side or the coated side which is coated with the capsule coating.

The carrageenan preferably includes λ carrageenan.

No polysaccharide thickener other than carrageenan is preferably contained.

Advantageous Effect of Invention

By containing an enteric property imparting agent in the coating side, the enteric capsule of the present invention has the enteric property without being restricted by the presence or absence of divalent or monovalent cations in the capsule content.

DESCRIPTION OF EMBODIMENTS

First, a typical enteric capsule will be explained below in which the enteric property is imparted to the capsule coating side so that the coating dissolves in the intestines to release the capsule content of the coated side.

Incidentally, the types of capsule formulation include a soft capsule, a seamless capsule, and a hard capsule, each of which has its unique characteristics. The present invention can be applied to all of the types.

Capsule Content

Materials that have conventionally used as a content of a gelatin-based capsule and materials that can be applied as a content of a gelatin-based capsule and will be conceived in future are to be applied as a content of the capsule of the present invention.

In the case of a soft capsule or a seamless capsule, a typical capsule content includes an oil or fat as a base material and an effective ingredient of a powder or liquid form contained therein. Examples of the oil or fat include a vegetable oil, such as soy bean oil, olive oil, and wheat germ oil, medium chain triglyceride (MCT), an oil or fat that is in a solid format around normal temperature, such as bees wax, monoacylglycerol (mono-gly), beef tallow, lard, and cacao butter, and a mixture thereof.

Examples of types of the effective ingredient include a medical ingredient, such as a bronchodilator and an allergy medicine in the case of a use purpose for an oral medicine, and a functional ingredient, such as docosahexaenoic acid, various vitamins, various extract powders in the case of that for a food. Incidentally, in terms of the solubility in oil, not only a material that readily dissolves in oil but also a material that poorly dissolves in oil may be used as long as its dispersibility is ensured.

In the case of a hard capsule, such an effective ingredient is often encapsulated as it is without being dispersed in an oil or fat. The form of the effective ingredient in this case is not limited to the powder or liquid form as mentioned above, and may include a gel form, a granule form, a tablet form, a pellet form, or a mixture thereof. In the case of a powder or granule form, as with the existing products, corn starch, dextrin, or the like may be incorporated as an excipient for improving flowability or the like, and a sucrose fatty acid ester, calcium stearate, magnesium stearate, or the like may be incorporated as a lubricant.

Capsule Coating

A first component of the base materials of the capsule coating is gelatin, and in the present invention, the capsule coating is, so to say, based on gelatin since gelatin accounts for the majority of the base materials.

Gelatin is derived from collagen, which is a main protein component of skin, bone, and sinew of cattle, sheep, pig, chicken, and fish, as the raw material. A gelatin derived from cattle bone, cattle skin, or pig skin is easily available as an industrial raw material, but the origin is not particularly limited.

However, the detail of the treatment is limited. Gelatin is a modified material of collagen obtained by treating such a raw material as mentioned above with an acid or alkali, followed by extraction with hot water. The modes for treatment include an acid treatment and an alkali treatment, but in the capsule coating of the present invention, an alkali-treated gelatin is intended to be used and an acid-treated gelatin is intentionally not incorporated.

The alkali treatment is generally achieved by liming, but not limited thereto.

Incidentally, gelatin has long been used as a base material of the capsule coating, but the gelatins that have been in the actual marketplace are acid-treated gelatins from the aspect of the cost. Although an indication of the ingredients on a product rarely refers to the detailed treatment on gelatin, the simple indication of "gelatin" means an acid-treated gelatin. The use of an alkali-treated gelatin is thus not a common knowledge.

The "gelation ability" of gelatin is maintained both in the acid treatment and in the alkali treatment, but gelatin is an ampholite containing both of an acidic and a basic amino acids. A majority of acid-treated gelatins have an isoelectric point of approximately 8 to 9 which is close to that of collagen because of a low deamidation rate, and the distribution of the isoelectric point is broad since the degree of the deamidation differs from molecule to molecule. In contrast, a majority of alkali-treated gelatins have an isoelectric point around 5 because of a deamidation in large part, and the isoelectric point distribution is sharp since the deamidation degree is uniform from molecule to molecule. Incidentally, the isoelectric point of a gelatin, as used in the present invention, means the pH when salt ions are completely removed from a gelatin solution, namely, the isoionic point.

The pH of the human gastric juice is generally about 1, and the pH of the intestinal juice is about 7. Accordingly, in the gastric juice having a low pH, an alkali-treated gelatin is positively (+) charged. On the other hand, in the intestinal juice having a high pH, an alkali-treated gelatin is negatively (−) charged. The present invention utilizes the property of change in electric charge of an alkali-treated gelatin between in the gastric environment and in the intestinal environment.

A second component of the base materials of the capsule coating is carrageenan.

Carrageenan is one kind of galactan having a sulfate group (SO3− group), and is known to exist in ret algae. Carrageenan is roughly classified into three types of κ (kappa) carrageenan, ι (iota) carrageenan, and λ (lambda) carrageenan by the difference in structure and the gelation characteristics, and the three types respectively have one, two, and three sulfate groups (SO3− groups) relative to two galactose groups. Due to the existence of a sulfate ester, carrageenan is always negatively (−) charged in a liquid having any pH. That is, even if the environment varies from a gastric environment to an intestinal environment, carrageenan is always negatively (−) charged.

Incidentally, regarding the gelation characteristics, the larger the number of the sulfate groups (SO3− groups), the lower the gelation ability. Thus, κ (kappa) carrageenan having one sulfate group (SO3−) and ι (iota) carrageenan having two sulfate groups (SO3−) have a gelation ability, whereas λ (lambda) carrageenan having three sulfate groups (SO3−) has no substantial gelation ability.

In the present invention, the above-described properties of carrageenan is utilized, and carrageenan is allowed to coexist with an alkali-treated gelatin which acts as the main base material of the coating.

Accordingly, in the gastric (aqueous) environment, an alkali-treated gelatin which is positively (+) charged coexists with a carrageenan which is negatively (−) charged, and amino groups (NH4+) in the gelatin react with the sulfate groups (SO3−) in the carrageenan so that the coating is insolubilized.

On the other hand, in the intestines (aqueous) environment, the alkali-treated gelatin negatively (−) charged coexists with the carrageenan negatively (−) charged, and the amino groups (NH4+) in the gelatin are repulsive to the sulfate groups (SO3−) in the carrageenan so that the coating quickly disintegrates or dissolves.

As described above, there are some kinds in carrageenan, and it is recommended in the present invention that λ carrageenan is used alone or in combination. The λ carrageenan has no gelation ability, which is thus expected to increase disintegration ability in the intestinal environment to enable rapid dissolution of the coating while ensuring filling adequacy by suppressing elevation of the gelation temperature of a coating solution prepared in production of a capsule formulation. When two or more kinds of carrageenan are used in combination, a blended raw material in which those are mixed in advance may be used.

Each kind of carrageenan may be a pure material, or one containing a standardized substance may be used. Examples of the standardized substance include one or more selected from the group consisting of a saccharide, such as sucrose, glucose, maltose, and lactose, and dextrin.

In terms of the relationship between the insolubilization of coating and the dissolution caused by the electrical charge, the incorporation ratio of the alkali-treated gelatin and the carrageenan is preferably 1 to 20 parts by mass of the carrageenan relative to 100 parts by mass of the alkali-treated gelatin. In this range, the effect of the electrical charge in the carrageenan can be substantially achieved, whereas increase in viscosity due to incorporation of the carrageenan which is one of polysaccharide thickeners is suppressed to a certain degree to easily ensure the filling adequacy.

As described above, carrageenan is one of polysaccharide thickeners, and other example of polysaccharide thickeners include xanthan gum, galactomannan (LBG), pectin, and sodium alginate. These have conventionally been sometimes added for other purposes, such as prevention of adhesion of the capsule coating and deformation of the capsule due to temperature change in storage or distribution, that is, enhancement of the thermal resistance, prevention of adhesion in the oral cavity and esophagus, enhancement in easy-to-swallow property, and improvement of texture. However, the polysaccharide thickener leads to increase in the viscosity of a coating solution. In particular, when carrageenan is contained in the coating side, the above purposes can also be achieved. Accordingly, no polysaccharide thickener other than carrageenan is preferably contained.

In addition, a film forming agent includes, besides gelatin, a non-gelatin-based material, such as hydroxypropylmethylcellulose (HPMC), a starch, agar, and the like. However, those are preferably intentionally not incorporated also in order not to lower the relative incorporation amount of gelatin.

In the capsule coating of the present invention, in addition the base materials including the alkali-treated gelatin and the carrageenan, a plasticizer, such as glycerol and sorbitol, which is needed for production of a capsule formulation, and furthermore, a colorant, a preservative, and a sweetener may be incorporated as needed.

Capsule Formulation Production Method

As the capsule coating side, the capsule coating base materials described above are dissolved together in water and stirred into a uniform coating solution. Then, a capsule content is filled and encapsulated therein while molding the capsule, thereby producing a capsule formulation.

The types of capsule formulation include a soft capsule, a seamless capsule, and a hard capsule, each of which has its unique characteristics. The coating solution can be formed into all the types by the same treatment as for an existing gelatin-based capsule.

In the above description, an enteric property imparting agent is incorporated into the coating side, but the present invention is not limited thereto and an enteric property imparting agent may be incorporated into the coated side.

For example, when there are an effective ingredient intended to be released in the stomach and an effective ingredient intended to be released in the intestines, a capsule formulation can be conceived in which the effective ingredient to be released in the stomach is incorporated in the coating side so as to dissolve in the stomach, and the effective ingredient to be released in the intestines is incorporated in the capsule content side together with an enteric property imparting agent so as to dissolve in the intestines.

Incidentally, the effective ingredient to be released in the stomach and the effective ingredient to be released in the intestines are not always different ingredients. For example, when the blood concentration of an (a certain) effective ingredient is intended to last long, the effective ingredient is desirably allowed to be released both in the stomach and in the intestines. When the effective ingredient is contained both in the coating side and in the coated side, it is possible that not all the effective ingredient is released in the stomach but the remaining effective ingredient is surely brought into the intestines and released in the intestines.

A multi-layered capsule and a single sphere capsule are exemplified as a capsule, and such capsules are encompassed within the present invention.

In a multi-layered capsule, one or more intermediate layers and a capsule content (core or nucleus) constitutes the coated side, and an enteric property imparting agent may be incorporated in the coated side. With such a multi-layered capsule, the following configuration can be used. When it is difficult to incorporate an effective ingredient to be released in the stomach into the coating side, the effective ingredient is incorporated in an intermediate layer close to the coating so that the coating dissolves in the stomach to expose the intermediate layer in the stomach. Also for an effective ingredient to be released in the intestines, the following configuration can similarly be used. When it is difficult to incorporate the effective ingredient in the capsule content together with an enteric property imparting agent, the enteric property imparting agent is incorporated in an intermediated layer and the effective ingredient is separately incorporated in the nucleus so that the intermediate layer dissolves in the intestines to release the content.

A capsule formulation of multi-layered capsule can be produced by an ordinary method as one kind of a seamless capsule, and therefore it is possible to realize the multi-layered capsules as described above.

In a single sphere capsule, the capsule coating and the capsule content are configured with the same composition, and can not be distinguished.

In the case where an effective ingredient to be absorbed in the intestines can be incorporated in the capsule coating together with an enteric property imparting agent with a focus only on the effective ingredient, such a form of single sphere capsule may be adopted.

EXAMPLES

Example 1

The following examples were implemented for verifying the capsule coating.

Components in various compositions for coating were put in water at 85° C. and stirred for 10 minutes to dissolve in water, whereby a uniform coating solution was prepared.

The viscosities were measurement results by a rotational viscometer (Brookfield viscometer).

The evaluation criteria of the filling adequacy of the coating solution were as follows.

Evaluation Criteria

Θ: Yield in filling is 90% or more.
○: Yield in filling is 70% or more.
Δ: Filling is possible.
X: Filling is not possible.

The enteric property test was a dissolution test implemented on a capsule formulation produced in the following manner using the first fluid (artificial gastric juice) in the Japanese Pharmacopeia and the second fluid (artificial intestinal juice) in the Japanese Pharmacopeia on the basis of the Japanese pharmacopeia, 16th Edition.

Soft Capsule

By a rotary-type rotational punching method, a MCT-filled capsule of the oval No. 6 (coating weight: 165 mg, content weight: 300 mg) was produced.

Seamless Capsule

By a dropping-in-liquid method, a MCT-filled capsule having a major axis of about 6 mmΦ (coating weight: 20 mg, content weight: 100 mg) was produced.

Hard Capsule

By an immersion method, a hollow capsule of the hard capsule No. 1 (hollow capsule weight: about 78 mg) was produced and then filled with corn starch.

The evaluation criteria of the enteric property were as follows based on the Japanese Pharmacopeia, 16th Edition.

First Fluid

Θ: All of 6 capsules do not disintegrate over 120 minutes.
○: 4 or 5 of 6 capsules do not disintegrate, and in a retest, 16 or more in 18 capsules do not disintegrate over 120 minutes.
Δ: 4 or 5 of 6 capsules do not disintegrate, and in a retest, 2 or more of 18 capsules disintegrate.
X: Dissolution starts immediately.

Second Fluid

Θ: All of 6 capsules disintegrate within 60 minutes.
○: 4 or 5 of 6 capsules disintegrate, and in a retest, 16 or more in 18 capsules disintegrate within 120 minutes.
Δ: 4 or 5 of 6 capsules disintegrate, and in a retest, 2 or more of 18 capsules do not disintegrate.
X: Do not disintegrate over 60 minutes.

TABLE 1

| General name | Raw material name | Sample 1 | Sample 2 | Sample 3 | Sample 4 | Sample 5 | Sample 6 | Sample 6-A | Sample 6-B |
|---|---|---|---|---|---|---|---|---|---|
| Acid-treated gelatin | | | | | | | | | |
| Alkali-treated gelatin | | 100 | 100 | 100 | 100 | 100 | 100 | 100 | 100 |
| κ Carrageenan | | 1 | 20 | | | | | | |
| ι Carrageenan | | | | 1 | 20 | | | | |
| λ Carrageenan | | | | | | 1 | 20 | 20 | 20 |
| Xanthan gum | | | | | | | | | |
| Galactomannan (LBG) | | | | | | | | | |
| Pectin | | | | | | | | | |
| Sodium alginate | | | | | | | | | |
| Glycerol | | 25 | 25 | 25 | 25 | 25 | 25 | 25 | 25 |
| | | 1 $SO_3$-group to 2 galactose groups | 1 $SO_3$-group to 2 galactose groups | 2 $SO_3$-groups to 2 galactose groups | 2 $SO_3$-groups to 2 galactose groups | 3 $SO_3$-groups to 2 galactose groups | 3 $SO_3$-groups to 2 galactose groups | 3 $SO_3$-groups to 2 galactose groups Content composition MCT 98% Potassium chloride 2% | 3 $SO_3$-groups to 2 galactose groups Content composition MCT 98% Calcium lactate 2% |
| Soft capsule coating solution | Purified water | 110 | 110 | 110 | 110 | 110 | 110 | 110 | 110 |
| | Viscosity (cP/75° C.) | 25000 | 28000 | 25000 | 26000 | 25000 | 36000 | 36000 | 36000 |
| | Filling adequacy | ⊖ | ⊖ | ⊖ | ⊖ | ⊖ | Δ | Δ | Δ |
| Seamless capsule coating solution | Purified water | 520 | 520 | 520 | 520 | 520 | 580 | 580 | 580 |
| | Viscosity (cP/75° C.) | 40 | 160 | 100 | 330 | 160 | 350 | 350 | 350 |
| | Filling adequacy | ⊖ | ⊖ | ⊖ | ○ | ⊖ | ○ | ○ | ○ |
| Hard capsule coating solution | Purified water | 310 | 310 | 310 | 310 | 310 | 310 | 310 | 310 |
| | Viscosity (cP/75° C.) | 1000 | 2500 | 1000 | 3900 | 1000 | 15100 | 15000 | 15200 |
| | Filling adequacy | ⊖ | ⊖ | ⊖ | ⊖ | ⊖ | Δ | Δ | Δ |
| | Aggregation or clouding | Not observed | Not observed | Not observed | Not observed | Not observed | Not observed | Not observed | Not observed |
| | Enteric property test 1st fluid | ○ | ⊖ | ○ | ⊖ | ○ | ⊖ | ⊖ | ⊖ |
| | 2nd fluid | ○ | ○ | ○ | ○ | ○ | ⊖ | ⊖ | ⊖ |

In the samples 1 to 6 (the present invention) shown in table 1, an alkali-treated gelatin and a carrageenan coexisted and the samples had moderate viscosities, satisfied the filling adequacy, and also satisfied adequacy in terms of the enteric property.

In particular, the sample 6 (λ carrageenan was incorporated) showed a good result in the enteric property test (second fluid), and dissolved completely.

In addition, for comparison with the sample 6, a sample 6-A (potassium chloride was incorporated into the capsule content) and a sample 6-B (calcium lactate was incorporated into the capsule content) were tested. The samples 6-A and 6-B contained divalent or monovalent cations in the capsule content and the mass ratio of MCT was reduced by the corresponding amount. These had the same configuration as the sample 6 except for the above point. The samples 6-A and 6-B also showed good results comparable with the sample 6. These results confirmed that the presence of divalent or monovalent cations has not adverse effect.

TABLE 2

| General name | Raw material name | Sample 7 | Sample 8 | Sample 9 | Sample 10 |
|---|---|---|---|---|---|
| Acid-treated gelatin | | | | | |
| Alkali-treated gelatin | | 100 | 100 | 100 | 100 |
| κ Carrageenan | | | | | |
| ι Carrageenan | | | | | |
| λ Carrageenan | | | | | |
| Xanthan gum | | 5 | | | |
| Galactomannan (LBG) | | | 5 | | |
| Pectin | | | | 5 | |
| Sodium alginate | | | | | 5 |
| Glycerol | | 25 | 25 | 25 | 25 |
| | | Confirmation of effect of other polysaccharides | | | |
| | | COO– group | Galactose group | COO– group | COO– group |

TABLE 2-continued

| | | Coating composition | | | |
|---|---|---|---|---|---|
| General name | Raw material name | Sample 7 | Sample 8 | Sample 9 | Sample 10 |
| Soft capsule coating solution | Purified water | 110 | 110 | 110 | 110 |
| | Viscosity (cP/75° C.) | 70000 | 50000 | 40000 | 40000 |
| | Filling adequacy | X | X | X | X |
| Seamless capsule coating solution | Purified water | 520 | 520 | 520 | 520 |
| | Viscosity (cP/75° C.) | 6000 | 4000 | 3000 | 3000 |
| | Filling adequacy | X | X | X | X |
| Hard capsule coating solution | Purified water | 310 | 310 | 310 | 310 |
| | Viscosity (cP/75° C.) | 24500 | 20000 | 20500 | 20600 |
| | Filling adequacy | X | X | X | X |
| | Aggregation or clouding | Not observed | Not observed | Not observed | Not observed |
| | Enteric property test 1st fluid | X | X | X | X |
| | 2nd fluid | — | — | — | — |

In the samples 7 to 10 (Comparative Examples) shown in Table 2, a polysaccharide thickener other than carrageenan was incorporated, and the viscosity excessively increased and the filling adequacy lowered. In addition, the characteristics as an ampholite of the gelatin were not utilized and the samples completely dissolved in the enteric property test (first fluid).

TABLE 3

| | | Coating composition | | | |
|---|---|---|---|---|---|
| General name | Raw material name | Sample 11 | Sample 12 | Sample 13 | Sample 14 |
| Acid-treated gelatin | | | | | |
| Alkali-treated gelatin | | 100 | 100 | 100 | 100 |
| κ Carrageenan | | | | | |
| ι Carrageenan | | | | | |
| λ Carrageenan | | 2.5 | 2.5 | 2.5 | 2.5 |
| Xanthan gum | | 2.5 | | | |
| Galactomannan (LBG) | | | 2.5 | | |
| Pectin | | | | 2.5 | |
| Sodium alginate | | | | | 2.5 |
| Glycerol | | 25 | 25 | 25 | 25 |
| | | Confirmation of effect of other polysaccharides by incorporating each into λ carrageenan showing high effect | | | |
| | | 3 SO3– groups to 2 galactose groups COO– group | 3 SO3– groups to 2 galactose groups Galactose group | 3 SO3– groups to 2 galactose groups COO– group | 3 SO3– groups to 2 galactose groups COO– group |
| Soft capsule coating solution | Purified water | 110 | 110 | 110 | 110 |
| | Viscosity (cP/75° C.) | 70000 | 50000 | 40000 | 40000 |
| | Filling adequacy | Δ | Δ | Δ | Δ |
| Seamless capsule coating solution | Purified water | 520 | 520 | 520 | 520 |
| | Viscosity (cP/75° C.) | 5000 | 4000 | 3000 | 2500 |
| | Filling adequacy | Δ | Δ | Δ | Δ |

TABLE 3-continued

| | | Coating composition | | | |
|---|---|---|---|---|---|
| General name | Raw material name | Sample 11 | Sample 12 | Sample 13 | Sample 14 |
| Hard capsule coating solution | Purified water | 310 | 310 | 310 | 310 |
| | Viscosity (cP/75° C.) | 30800 | 24600 | 18300 | 15000 |
| | Filling adequacy | Δ | Δ | Δ | Δ |
| | Aggregation or clouding | Not observed | Not observed | Not observed | Not observed |
| | Enteric property test | 1st fluid | Δ | Δ | Δ | Δ |
| | | 2nd fluid | Δ | Δ | Δ | Δ |

In the samples 11 to 14 (the present invention) shown in Table 3, another polysaccharide thickener was incorporated in addition to λ carrageenan, and the filling adequacy was lowered by increase in the viscosity. In the enteric property test, the samples slightly dissolved in the first fluid, and in contrast, slightly remained in the second fluid.

coating solution, a negatively (−) charged carrageenan coexisted with a positively (+) charged acid-treated gelatin, and aggregation or clouding was caused by a neutralization reaction of the amino groups (NH4+) in the gelatin with the sulfate groups (SO3−) in carrageenan. Thus, the gelation

TABLE 4

| | | Coating composition | | | | | |
|---|---|---|---|---|---|---|---|
| General name | Raw material name | Sample 15 | Sample 16 | Sample 17 | Sample 18 | Sample 19 | Sample 20 |
| Acid-treated gelatin | | 100 | 100 | 100 | 100 | 100 | 100 |
| Alkali-treated gelatin | | | | | | | |
| κ Carrageenan | | 1 | 20 | | | | |
| ι Carrageenan | | | | 1 | 20 | | |
| λ Carrageenan | | | | | | 1 | 20 |
| Xanthan gum | | | | | | | |
| Galactomannan (LBG) | | | | | | | |
| Pectin | | | | | | | |
| Sodium alginate | | | | | | | |
| Glycerol | | 25 | 25 | 25 | 25 | 25 | 25 |
| | | 1 SO3− group to 2 galactose groups | 1 SO3− group to 2 galactose groups | 2 SO3− groups to 2 galactose groups | 2 SO3− groups to 2 galactose groups | 3 SO3− groups to 2 galactose groups | 3 SO3− groups to 2 galactose groups |
| Soft capsule coating solution | Purified water | 110 | 110 | 110 | 110 | 110 | 110 |
| | Viscosity (cP/75° C.) | 25000 | 25000 | 25000 | 30000 | 25000 | 36000 |
| | Filling adequacy | Δ | Δ | Δ | Δ | Δ | X |
| Seamless capsule coating solution | Purified water | 520 | 520 | 520 | 520 | 520 | 580 |
| | Viscosity (cP/75° C.) | 50 | 250 | 100 | 700 | 250 | 580 |
| | Filling adequacy | Δ | Δ | Δ | X | Δ | X |
| Hard capsule coating solution | Purified water | 310 | 310 | 310 | 310 | 310 | 310 |
| | Viscosity (cP/75° C.) | 1050 | 2000 | 1000 | 5400 | 1000 | 15500 |
| | Filling adequacy | Δ | Δ | Δ | Δ | Δ | X |
| | Aggregation or clouding | Observed | Observed | Observed | Observed | Observed | Observed |
| | Enteric property test | 1st fluid | Δ | ⊖ | Δ | ○ | ○ | ○ |
| | | 2nd fluid | X | X | X | X | X | X |

In the samples 15 to 20 (Comparative Examples) shown in Table 4, an acid-treated gelatin was incorporated in place of an alkali-treated gelatin. In the stage of producing the coating solution, a negatively (−) charged carrageenan coexisted with a positively (+) charged acid-treated gelatin, and aggregation or clouding was caused by a neutralization reaction of the amino groups (NH4+) in the gelatin with the sulfate groups (SO3−) in carrageenan. Thus, the gelation ability of the gelatin was impaired and the filling adequacy decreased. In the enteric property test (second fluid), each sample mostly remained not to be dissolved.

TABLE 5

Coating composition

| General name | Raw material name | Sample 21 | Sample 22 | Sample 23 | Sample 24 | Sample 25 | Sample 26 | Sample 27 | Sample 28 | Sample 29 | Sample 30 |
|---|---|---|---|---|---|---|---|---|---|---|---|
| Acid-treated gelatin | | | | | | | | | | | |
| Alkali-treated gelatin | | 100 | 100 | 100 | 100 | 100 | 100 | 100 | 100 | 100 | 100 |
| κ Carrageenan | | | | | | | | | | | |
| ι Carrageenan | | | | | | | | | | | |
| λ Carrageenan | | 0.4 | 0.5 | 1.5 | 2 | 2.5 | 3 | 3.5 | 4 | 10 | 30 |
| Xanthan gum | | | | | | | | | | | |
| Galactomannan (LBG) | | | | | | | | | | | |
| Pectin | | | | | | | | | | | |
| Sodium alginate | | | | | | | | | | | |
| Glycerol | | 25 | 25 | 25 | 25 | 25 | 25 | 25 | 25 | 25 | 25 |
| | | 1 SO3– group to 2 galactose groups | 2 SO3– groups to 2 galactose groups | 3 SO3– groups to 2 galactose groups | 3 SO3– groups to 2 galactose groups | 3 SO3– groups to 2 galactose groups | 3 SO3– groups to 2 galactose groups | 3 SO3– groups to 2 galactose groups | 3 SO3– groups to 2 galactose groups | 3 SO3– groups to 2 galactose groups | 3 SO3– groups to 2 galactose groups |
| Soft capsule coating solution | Purified water | 110 | 110 | 110 | 110 | 110 | 110 | 110 | 110 | 110 | 110 |
| | Viscosity (cP/75° C.) | 24000 | 24000 | 24000 | 24000 | 25000 | 26000 | 28000 | 30000 | 32000 | 38000 |
| | Filling adequacy | ⊖ | ⊖ | ⊖ | ⊖ | ⊖ | ⊖ | ○ | ○ | ○ | Δ |
| Seamless capsule coating solution | Purified water | 520 | 520 | 520 | 520 | 520 | 520 | 520 | 580 | 580 | 580 |
| | Viscosity (cP/75° C.) | 120 | 120 | 188 | 282 | 300 | 438 | 572 | 280 | 320 | 580 |
| | Filling adequacy | ⊖ | ⊖ | ⊖ | ⊖ | ⊖ | ⊖ | ○ | ○ | ○ | Δ |
| Hard capsule coating solution | Purified water | 310 | 310 | 310 | 310 | 310 | 310 | 310 | 310 | 310 | 310 |
| | Viscosity (cP/75° C.) | 1100 | 1100 | 1200 | 2600 | 3300 | 3780 | 8100 | 10000 | 15000 | 21000 |
| | Filling adequacy | ⊖ | ⊖ | ⊖ | ⊖ | ⊖ | ⊖ | ○ | Δ | Δ | Δ |
| | Aggregation or clouding | Not observed | Not observed | Not observed | Not observed | Not observed | Not observed | Not observed | Not observed | Not observed | Not observed |
| | Enteric property test 1st fluid | ○ | ○ | ⊖ | ○ | ⊖ | ⊖ | ⊖ | ⊖ | ⊖ | ⊖ |
| | 2nd fluid | ○ | ○ | ⊖ | ⊖ | ⊖ | ⊖ | ⊖ | ⊖ | ⊖ | ⊖ |

In the samples 21 to 30 (the present invention) shown in Table 5, the incorporated amount of λ carrageenan was set at various values. When the amount was 1.0 part by mass or more, high levels of enteric property were exhibited.

TABLE 6

Coating composition

| General name | Raw material name | Sample 31 | Sample 32 | Sample 33 | Sample 34 |
|---|---|---|---|---|---|
| Acid-treated gelatin | | | | | |
| Alkali-treated gelatin | | 100 | 100 | 100 | 100 |
| κ Carrageenan | | 5 | | 5 | |
| ι Carrageenan | | | 5 | 5 | 3.5 |
| λ Carrageenan | | 5 | 5 | | 3.5 |
| Xanthan gum | | | | | 3.5 |
| Galactomannan (LBG) | | | | | |

TABLE 6-continued

| | | Coating composition | | | |
|---|---|---|---|---|---|
| General name | Raw material name | Sample 31 | Sample 32 | Sample 33 | Sample 34 |
| Pectin | | | | | |
| Sodium alginate | | | | | |
| Glycerol | | 25 | 25 | 25 | 25 |
| | | κ | ι | κ | κ |
| | | 1 SO3– group to 2 galactose groups | 2 SO3– groups to 2 galactose groups | 1 SO3– group to 2 galactose groups | 1 SO3– group to 2 galactose groups |
| | | | | | ι |
| | | | | | 2 SO3– groups to 2 galactose groups |
| | | λ | λ | ι | |
| | | 3 SO3– groups to 2 galactose groups | 3 SO3– groups to 2 galactose groups | 2 SO3– groups to 2 galactose groups | λ |
| | | | | | 3 SO3– groups to 2 galactose groups |
| Soft capsule coating solution | Purified water | 110 | 110 | 110 | 110 |
| | Viscosity (cP/75° C.) | 25000 | 26000 | 25000 | 2500 |
| | Filling adequacy | ⊖ | ⊖ | ⊖ | ⊖ |
| Seamless capsule coating solution | Purified water | 580 | 580 | 580 | 580 |
| | Viscosity (cP/75° C.) | 180 | 240 | 120 | 200 |
| | Filling adequacy | ⊖ | ⊖ | ⊖ | ⊖ |
| Hard capsule coating solution | Purified water | 310 | 310 | 310 | 310 |
| | Viscosity (cP/75° C.) | 1200 | 1100 | 850 | 900 |
| | Filling adequacy | ⊖ | ⊖ | ⊖ | ⊖ |
| | Aggregation or clouding | Not observed | Not observed | Not observed | Not observed |
| | Enteric property test 1st fluid | ⊖ | ⊖ | ⊖ | ⊖ |
| | 2nd fluid | ⊖ | ⊖ | ○ | ⊖ |

In the samples 31 to 34 (the present invention) shown in Table 6, two types of carrageenan were used in combination, and when λ carrageenan was used in combination with κ carrageenan or ι carrageenan, the effect of incorporation of λ carrageenan was sufficiently achieved, and the viscosity increase at the stage of coating solution was suppressed, and high levels of filling adequacy were exhibited and high levels of enteric property were exhibited.

Example 2

An enteric property test was conducted on tri-layered seamless capsules (coating portion, intermediate layer, nucleus) having the following compositions.

TABLE 7

| | | Coating composition (parts by mass) | | Intermediate layer composition (parts by mass) | | Nucleus composition (parts by mass) | |
|---|---|---|---|---|---|---|---|
| Sample 35 | Gelatin | 100 | | Alkali-treated gelatin | 100 | Middle chain triglyceride | 100 |
| | Glycerol | 25 | | λ Carrageenan | 10 | | |
| | Water | 375 | | Glycerol | 25 | | |
| | Solid content | 25% | | Water | 540 | | |
| | Mass of capsule | | | Solid content | 20% | | |
| | Coating | 15 | | | | | |
| | Intermediate layer | 10 | | | | | |
| | Nucleus | 90 | | | | | |
| | Total | 115 (mg) | | | | | |
| Sample 36 | Gelatin | 100 | | Coconade ML | 100 | Alkali-treated gelatin | 100 |
| | Glycerol | 25 | | | | λ Carrageenan | 10 |
| | Water | 375 | | | | Glycerol | 25 |
| | Solid content | 25% | | | | Water | 540 |
| | Mass of capsule | | | | | | |

TABLE 7-continued

| Coating composition (parts by mass) | | Intermediate layer composition (parts by mass) | Nucleus composition (parts by mass) | |
|---|---|---|---|---|
| Coating | 15 | | Solid content | 25% |
| Intermediate layer | 95 | | | |
| Nucleus | 5 | | | |
| Total | 115 (mg) | | | |

TABLE 8

| | First fluid (artificial gastric juice) | Second fluid (artificial intestinal juice) |
|---|---|---|
| Sample 35 | Coating portion: 8 min disintegration<br>Intermediate layer: 120 min no disintegration<br>Nucleus: 120 min no disintegration | Coating portion: 12 min disintegration<br>Intermediate layer: 12 min disintegration<br>Nucleus: 120 min no disintegration |
| Sample 36 | Coating portion: 8 min disintegration<br>Intermediate layer: 9 min disintegration<br>Nucleus: 10 min disintegration | Coating portion: 8 min disintegration<br>Intermediate layer: 9 min disintegration<br>Nucleus: 15 min disintegration |

Both the samples 35 to 36 (the present invention) shown in Table 8 showed high levels of enteric property.

The invention claimed is:

1. A gelatin-based enteric capsule, comprising an alkali-treated gelatin and a carrageenan as an enteric property imparting agent in a capsule coating side or in a coated side coated with a capsule coating, but comprising no gelatin other than the alkali-treated gelatin, and no counter ion to be bound to the carrageenan, wherein:
   in an aqueous gastric environment, amino groups in the alkali-treated gelatin react with the sulfate groups in the carrageenan so that the capsule coating side or coated side containing the alkali-treated gelatin and the carrageenan is insolubilized in a gastric aqueous environment; and
   in an aqueous intestinal environment, the amino groups in the alkali-treated gelatin are repulsive to the sulfate groups in the carrageenan so that the capsule coating side or coated side containing the alkali-treated gelatin and the carrageenan disintegrates or dissolves.

2. The enteric capsule according to claim 1, wherein the carrageenan contains λ carrageenan.

3. The enteric capsule according to claim 2, comprising no polysaccharide thickener other than carrageenan as an enteric property imparting agent.

4. The enteric capsule according to claim 1, which is a soft capsule, a seamless capsule, or a hard capsule.

5. The enteric capsule according to claim 1, which is a soft capsule or a seamless capsule.

6. The enteric capsule according to claim 4, wherein the alkali-treated gelatin and the carrageenan are contained in the coated side as an enteric property imparting agent.

7. The enteric capsule according to claim 2, which is a soft capsule, a seamless capsule, or a hard capsule.

8. The enteric capsule according to claim 3, which is a soft capsule, a seamless capsule, or a hard capsule.

9. The enteric capsule according to claim 2, which is a soft capsule or a seamless capsule.

10. The enteric capsule according to claim 3, which is a soft capsule or a seamless capsule.

11. The enteric capsule according to claim 7, wherein the alkali-treated gelatin and the carrageenan are contained in the coated side as an enteric property imparting agent.

12. The enteric capsule according to claim 8, wherein the alkali-treated gelatin and the carrageenan are contained in the coated side as an enteric property imparting agent.

13. The enteric capsule according to claim 5, wherein the alkali-treated gelatin and the carrageenan are contained in the coated side as an enteric property imparting agent.

14. The enteric capsule according to claim 9, wherein the alkali-treated gelatin and the carrageenan are contained in the coated side as an enteric property imparting agent.

15. The enteric capsule according to claim 10, wherein the alkali-treated gelatin and the carrageenan are contained in the coated side as an enteric property imparting agent.

* * * * *